United States Patent
MacDonald et al.

(10) Patent No.: US 10,568,771 B2
(45) Date of Patent: Feb. 25, 2020

(54) TRAUMATIC WOUND DRESSING SYSTEM WITH CONFORMAL COVER

(71) Applicants: Avent, Inc., Alpharetta, GA (US); John Gavin MacDonald, Decatur, GA (US); Ramanathan S. Lalgudi, Westerville, OH (US); Karien J. Rodriguez, Roswell, GA (US); Reade Harpham, Columbus, OH (US); Stephanie Kute, Columbus, OH (US)

(72) Inventors: John Gavin MacDonald, Decatur, GA (US); Ramanathan S. Lalgudi, Westerville, OH (US); Karien J. Rodriguez, Roswell, GA (US); Reade Harpham, Columbus, OH (US); Stephanie Kute, Columbus, OH (US); Alison Salyer Bagwell, Alpharetta, GA (US); Brian Joseph Cuevas, Cumming, GA (US)

(73) Assignee: Avent, Inc., Alpharetta, GA (US)

( * ) Notice: Subject to any disclaimer, the term of this patent is extended or adjusted under 35 U.S.C. 154(b) by 201 days.

(21) Appl. No.: 15/113,123

(22) PCT Filed: Jan. 23, 2015

(86) PCT No.: PCT/US2015/012603
§ 371 (c)(1),
(2) Date: Jul. 21, 2016

(87) PCT Pub. No.: WO2015/112810
PCT Pub. Date: Jul. 30, 2015

(65) Prior Publication Data
US 2017/0007461 A1    Jan. 12, 2017

Related U.S. Application Data

(60) Provisional application No. 61/931,186, filed on Jan. 24, 2014.

(51) Int. Cl.
*A61F 13/00* (2006.01)
*A61M 1/00* (2006.01)
*A61L 15/44* (2006.01)

(52) U.S. Cl.
CPC .. *A61F 13/00068* (2013.01); *A61F 13/00029* (2013.01); *A61F 13/00038* (2013.01);
(Continued)

(58) Field of Classification Search
CPC .......... A61F 13/00068; A61F 13/00029; A61F 13/00038; A61F 13/00042;
(Continued)

(56) References Cited

U.S. PATENT DOCUMENTS

| 4,798,603 A | 1/1989 | Meyer et al. |
| 4,856,504 A | 8/1989 | Yamamoto et al. |

(Continued)

FOREIGN PATENT DOCUMENTS

| JP | 2010000159 A | 1/2010 |
| JP | 2012236628 A | 12/2012 |

(Continued)

OTHER PUBLICATIONS

International Search Report and Written Opinion for PCT/US2015/012603, dated Apr. 1, 2015, 7 pages.

*Primary Examiner* — Adam Marcetich
*Assistant Examiner* — Jessica R Arble
(74) *Attorney, Agent, or Firm* — Dority & Manning, P.A.

(57) ABSTRACT

A wound dressing system that includes a conformal cover and an infusion pump is provided. The cover includes a fluid port and an oxygen catalyst. The infusion pump is configured to deliver a bioactive liquid to the cover via the fluid port. The liquid includes an oxygen precursor. Upon combination, the oxygen catalyst and precursor react to form oxygen. A method of applying a wound dressing system (Continued)

including a bioactive powder, a bioactive liquid, and a conformal cover to a wound site is also provided. The method includes applying the powder to the wound site; securing the cover around the wound site, where the cover includes an oxygen catalyst and a fluid port; and delivering the bioactive liquid to at least an inner layer of the cover via the fluid port, where the bioactive liquid includes an oxygen precursor.

17 Claims, 4 Drawing Sheets

(52) U.S. Cl.
CPC .. *A61F 13/00042* (2013.01); *A61F 13/00046* (2013.01); *A61F 13/00063* (2013.01); *A61L 15/44* (2013.01); *A61M 1/0058* (2013.01); *A61M 1/0072* (2014.02); *A61L 2300/11* (2013.01)

(58) Field of Classification Search
CPC ......... A61F 13/00046; A61F 13/00063; A61L 2300/102; A61L 2300/104; A61L 2300/106; A61L 2300/11; A61L 2300/254
See application file for complete search history.

(56) References Cited

U.S. PATENT DOCUMENTS

| | | |
|---|---|---|
| 5,030,375 A | 7/1991 | Sigl et al. |
| 5,599,585 A | 2/1997 | Cohen |
| 5,730,994 A | 3/1998 | Askill et al. |
| 5,792,090 A | 8/1998 | Ladin |
| 5,807,563 A | 9/1998 | Askill et al. |
| 6,000,403 A | 12/1999 | Cantwell |
| 6,015,764 A | 1/2000 | McCormack et al. |
| 6,020,047 A | 2/2000 | Everhart |
| 6,045,900 A | 4/2000 | Haffner et al. |
| 6,103,647 A | 8/2000 | Shultz et al. |
| 6,111,163 A | 8/2000 | McCormack et al. |
| 6,172,276 B1 | 1/2001 | Hetzler et al. |
| 6,348,258 B1 | 2/2002 | Topolkaraev et al. |
| 6,485,733 B1 | 11/2002 | Huard et al. |
| 6,517,848 B1 | 2/2003 | Huard et al. |
| 6,521,241 B1 | 2/2003 | Minerath, III et al. |
| 6,551,607 B1 | 4/2003 | Minerath, III et al. |
| 6,627,564 B1 | 9/2003 | Morman et al. |
| 6,764,988 B2 | 7/2004 | Koenig et al. |
| 6,767,342 B1 | 7/2004 | Cantwell |
| 6,794,024 B1 | 9/2004 | Walton et al. |
| 6,797,856 B1 | 9/2004 | Kolb et al. |
| 6,822,135 B2 | 11/2004 | Soerens et al. |
| 6,887,496 B2 | 5/2005 | Koenig et al. |
| 6,936,035 B2 | 8/2005 | Rake et al. |
| 6,981,967 B2 | 1/2006 | Massengale et al. |
| 7,014,630 B2 | 3/2006 | Rosati |
| 7,160,553 B2 | 1/2007 | Gibbins et al. |
| 7,235,263 B2 | 6/2007 | Koenig et al. |
| 7,268,104 B2 | 9/2007 | Krzysik et al. |
| 7,335,713 B2 | 2/2008 | Land et al. |
| 7,422,712 B2 | 9/2008 | DeLucia et al. |
| 7,438,711 B2 | 10/2008 | Deniega et al. |
| 7,465,291 B2 | 12/2008 | Massengale |
| 7,527,609 B2 | 5/2009 | Deniega et al. |
| 7,547,302 B2 | 6/2009 | Porto et al. |
| 7,569,045 B2 | 8/2009 | Deniega et al. |
| 7,576,255 B2 | 8/2009 | Gibbins et al. |
| 7,642,397 B2 | 1/2010 | Cohen et al. |
| 7,666,824 B2 | 2/2010 | Krzysik et al. |
| 7,762,045 B2 | 7/2010 | Rosati |
| 7,813,807 B2 | 10/2010 | Franklin |
| 7,959,623 B2 | 6/2011 | Massengale |
| 8,075,537 B2 | 12/2011 | Franklin et al. |
| 8,110,215 B2 | 2/2012 | Koenig et al. |
| 8,166,731 B2 | 5/2012 | Rosati |
| 8,192,841 B2 | 6/2012 | Amundson et al. |
| 8,203,029 B2 | 6/2012 | Gibbons et al. |
| 8,293,965 B2 | 10/2012 | McMaken et al. |
| 8,308,688 B2 | 11/2012 | Valle et al. |
| 8,328,771 B2 | 12/2012 | Massengale |
| 8,361,553 B2 | 1/2013 | Karandikar et al. |
| 8,439,862 B2 | 5/2013 | Massengale |
| 8,475,560 B2 | 7/2013 | Gann et al. |
| 8,505,545 B2 | 8/2013 | Conquergood et al. |
| 8,545,951 B2 | 10/2013 | Yahiaoui et al. |
| 8,551,517 B2 | 10/2013 | Hoffman et al. |
| 8,679,523 B2 | 3/2014 | Gibbins et al. |
| 8,900,209 B2 | 12/2014 | Rosati |
| 8,901,188 B2 | 12/2014 | Karandikar et al. |
| 2001/0031938 A1 | 10/2001 | DeLucia et al. |
| 2002/0006887 A1 | 1/2002 | Radwanski et al. |
| 2002/0022050 A1 | 2/2002 | Anderson et al. |
| 2002/0111576 A1 | 8/2002 | Greene et al. |
| 2003/0040691 A1 | 2/2003 | Griesbach, III et al. |
| 2003/0127767 A1 | 7/2003 | Potts et al. |
| 2003/0203009 A1 | 10/2003 | MacDonald |
| 2004/0010215 A1 | 1/2004 | Gibbins et al. |
| 2004/0120915 A1 | 6/2004 | Yang et al. |
| 2004/0120921 A1 | 6/2004 | Quincy, III et al. |
| 2005/0058711 A1 | 3/2005 | Massengale et al. |
| 2005/0226916 A1* | 10/2005 | Cochrum .......... A61F 13/00034 424/445 |
| 2005/0251084 A1 | 11/2005 | Rosati |
| 2005/0267424 A1 | 12/2005 | Eriksson et al. |
| 2006/0003649 A1 | 1/2006 | Runge et al. |
| 2006/0036222 A1 | 2/2006 | Cohen et al. |
| 2006/0036223 A1 | 2/2006 | Baldwin et al. |
| 2006/0067964 A1 | 3/2006 | Koenig et al. |
| 2006/0121101 A1 | 6/2006 | Ladizinsky |
| 2006/0140994 A1 | 6/2006 | Bagwell et al. |
| 2006/0147502 A1 | 7/2006 | Koenig et al. |
| 2006/0200100 A1 | 9/2006 | Rosati |
| 2007/0003603 A1 | 1/2007 | Karandikar et al. |
| 2007/0044801 A1 | 3/2007 | Mathis et al. |
| 2007/0048344 A1 | 3/2007 | Yahiaoui et al. |
| 2007/0048345 A1 | 3/2007 | Huang et al. |
| 2007/0048356 A1 | 3/2007 | Schorr et al. |
| 2007/0134303 A1* | 6/2007 | Yahiaoui .............. A61F 13/104 424/443 |
| 2007/0141130 A1 | 6/2007 | Villanueva et al. |
| 2007/0148459 A1 | 6/2007 | Joseph et al. |
| 2007/0149435 A1 | 6/2007 | Koenig et al. |
| 2007/0254044 A1 | 11/2007 | Karandikar et al. |
| 2007/0292490 A1 | 12/2007 | Negrouk et al. |
| 2007/0293800 A1 | 12/2007 | McMaken et al. |
| 2008/0021373 A1 | 1/2008 | Rosati |
| 2008/0076722 A1* | 3/2008 | Roberts .................. A61K 31/70 514/23 |
| 2008/0108268 A1 | 5/2008 | Little et al. |
| 2008/0132438 A1 | 6/2008 | Hoffman et al. |
| 2009/0014009 A1 | 1/2009 | Chen et al. |
| 2009/0035342 A1 | 2/2009 | Karandikar et al. |
| 2009/0099531 A1 | 4/2009 | Griesbach, III |
| 2009/0099532 A1 | 4/2009 | Cuevas et al. |
| 2009/0202617 A1 | 8/2009 | Ward et al. |
| 2010/0038280 A1 | 2/2010 | Franklin et al. |
| 2010/0041998 A1 | 2/2010 | Postel |
| 2010/0063462 A1 | 3/2010 | Postel et al. |
| 2010/0087946 A1 | 4/2010 | Postel et al. |
| 2010/0190004 A1 | 7/2010 | Gibbins et al. |
| 2011/0135702 A1 | 6/2011 | Hoffman et al. |
| 2011/0184357 A1* | 7/2011 | Robinson .......... A61F 13/00068 604/290 |
| 2011/0213319 A1 | 9/2011 | Blott et al. |
| 2011/0257610 A1 | 10/2011 | Franklin |
| 2011/0257617 A1 | 10/2011 | Franklin |
| 2011/0282259 A1 | 11/2011 | Postel et al. |
| 2012/0016306 A1* | 1/2012 | Lee ....................... A61M 5/145 604/153 |
| 2012/0059301 A1 | 3/2012 | Franklin |
| 2012/0183674 A1 | 7/2012 | Bonn-Savage et al. |
| 2012/0240728 A1 | 9/2012 | Gann et al. |

(56) References Cited

U.S. PATENT DOCUMENTS

| | | | |
|---|---|---|---|
| 2012/0265124 A1 | 10/2012 | Karandikar et al. | |
| 2012/0322903 A1 | 12/2012 | Karandikar et al. | |
| 2013/0085435 A1* | 4/2013 | Murphy | A61K 33/30 602/46 |
| 2013/0164334 A1 | 6/2013 | Quincy, III et al. | |
| 2013/0396630 | 11/2013 | Franklin | |
| 2014/0046273 A1* | 2/2014 | Kang | A61M 35/003 604/290 |
| 2014/0276513 A1 | 9/2014 | MacDonald et al. | |
| 2014/0336557 A1* | 11/2014 | Durdag | A61L 15/26 602/48 |
| 2015/0017225 A1* | 1/2015 | Hubbell | A61L 15/64 424/444 |

FOREIGN PATENT DOCUMENTS

| | | |
|---|---|---|
| WO | WO 2009/102487 A2 | 8/2009 |
| WO | WO 2011/091045 A2 | 7/2011 |
| WO | WO 2015/112807 A1 | 7/2015 |

\* cited by examiner

TRAUMATIC WOUND DRESSING SYSTEM WITH CONFORMAL COVER

RELATED APPLICATIONS

The present application is the national stage entry of international Patent Application No, PCT/US2015/012603 having a filing date of Jan. 23, 2015, which claims priority to U.S. Provisional Application Ser. No. 61/931,186, filed on Jan. 24, 2014, both of which are incorporated herein in their entirety by reference thereto.

BACKGROUND

Wound and surgical dressings are often used to treat, cover, and protect wounds and surgical incisions. Wound and surgical dressings come in various forms. For example, for simple cuts, adhesive bandages are typically used. Cotton gauze is also commonly used to cover wounds and surgical incisions. For more serious wounds and surgical incisions, the wound or surgical dressing may include multiple layers of fibrous material with a fluid impervious layer or back sheet to prevent exudates from seeping through the dressing.

Typically, medicaments are often manually applied to the wound or surgical dressing before positioning on a wound or surgical incision. A medicament is a medicinal substance or agent. The medicaments may include, for instance, an antimicrobial agent or antibiotic agent to encourage healing. Antiseptics are also commonly applied to prevent infection.

Catastrophic and traumatic injuries, however, such as limb loss due to bomb blasts, severe burns, and natural disasters require more robust acute treatments to prevent further contamination by debris, mitigate infection, retain body fluids, and prevent heat loss, particularly if surgical care is distant in time or geography.

As such, a need currently exists for a wound dressing system that stabilizes the wound and prevents deterioration of the wound. Such a system can provide a barrier to the environment, can remove or prevent the growth of microorganisms, such as bacteria, and can provide barriers and or absorbency to combat bodily fluid loss, among other desired outcomes of its use.

SUMMARY

Described herein is an innovative medical technology solution particularly useful for service members who suffer the loss of a limb or a severe burn in the field. Currently corpsman and medical personnel are limited to sterile dressings, gauze wraps, ace bandages and in some cases plastic cling-type wrap to dress and protect a severed limb. These types of dressings can provide an exterior covering and keep the mangled limb together, but such dressings do little to promote healing and save valuable tissue. The use of these dressings, coupled with the extended time it often takes to move the casualty to a treatment facility (sometimes 72 hours), result in additional challenges in the form of infection and dead tissue that the battalion surgeons and other medical professionals must address. The traumatic wound dressing system described herein is designed to immediately facilitate the healing process from the point of injury to the initial treatment facility and during lengthy transits from the location of injury to established hospitals. The traumatic wound dressing system described herein is designed to be used in conjunction with a tourniquet to preserve as much of the severed limb as possible, particularly during what is referred to as the 'Golden Hour' after the injury. The traumatic wound dressing system can include a bioactive wrap to prevent infection, oxygen enriched fluid to preserve tissue, and pain medication for comfort. The wound dressing system includes an exterior conformal cover that protects the wound, contains precious body fluids, helps prevent heat loss, and enables the corpsman to administer additional pharmaceuticals during transit without removal of the entire wrap. The wrap may be a nonwoven composite. It is believed that none of these characteristics are currently available in one device. For instance, currently the M9 Medical Bag contains seven different items to do what the traumatic wound dressing system of the present disclosure does as a single unit. This system will reduce the need for multiple items and ultimately lighten the load the individual corpsman and medic is required to carry. The result will be a lighter load for the corpsman, less loss of valuable tissue, and a more comfortable and stable patient during transit to a medical treatment facility.

In one particular embodiment, the present disclosure is directed to a wound dressing system that includes a conformal cover and an infusion pump. The conformal cover includes a fluid port and an oxygen catalyst. The infusion pump is configured to deliver a bioactive liquid to the conformal cover via the fluid port, and the bioactive liquid includes an oxygen precursor.

In one particular embodiment, the conformal cover can be configured to form a sleeve around a wound site.

In another embodiment, the oxygen catalyst can include a nanoparticle metal, a carbonate, a copper compound, catalase, peroxidase, manganese dioxide, iodide, potassium iodine, or a combination thereof. Further, the nanoparticle metal can be silver.

In yet another embodiment, the bioactive liquid further can include a hemostatic agent, an antimicrobial agent, a biotoxin sequestrant, pain medication, a debridement agent, or a combination thereof.

In still another embodiment, the oxygen precursor includes a peroxide. The peroxide can include hydrogen peroxide, mannitol peroxide, urea peroxide, an organic peroxide, or a combination thereof.

In a further embodiment, the oxygen catalyst and the oxygen precursor are configured to form oxygen when combined.

In an additional embodiment, the wound dressing system of the present disclosure can include a bioactive powder. The bioactive powder can include a hemostatic agent, an antimicrobial agent, a biotoxin sequestrant, pain medication, a debridement agent, or a combination thereof.

In yet another embodiment, the conformal cover can be a nonwoven composite. In another embodiment, the conformal cover may include an outer protective layer. In still another embodiment, the conformal cover can include an inner absorbent layer, wherein the inner absorbent layer is positioned adjacent the wound site when the conformal cover is positioned around the wound site. In another embodiment, the conformal cover can include an elastic layer, a breathable layer, or a combination thereof.

In a further embodiment, the infusion pump of the wound dressing system of the present disclosure can be elastomeric.

In another embodiment, the present disclosure is directed to a method of applying a wound dressing system comprising a bioactive powder, a bioactive liquid, and a conformal cover to a wound site. The method includes applying the bioactive powder to the wound site; securing the conformal cover around the wound site, wherein the conformal cover includes an oxygen catalyst and a fluid port; and delivering the bioactive liquid to at least an inner layer of the conformal cover via the fluid port, wherein the bioactive liquid includes an oxygen precursor.

In one particular embodiment, oxygen is formed when the oxygen precursor contacts the oxygen catalyst. In another embodiment, the oxygen precursor can include a peroxide. In still another embodiment, the oxygen catalyst can include a nanoparticle metal, a carbonate, a copper compound, catalase, peroxidase, manganese dioxide, iodide, potassium iodine, or a combination thereof.

In yet another embodiment, the infusion pump can deliver the bioactive liquid to the interior of the conformal cover.

In a further embodiment, the conformal cover can be secured via one or more cinch straps.

Other features and aspects of the present disclosure are discussed in greater detail below.

BRIEF DESCRIPTION OF THE DRAWINGS

The foregoing and other features and aspects of the present disclosure and the manner of attaining them will become more apparent, and the disclosure itself will be better understood by reference to the following description, appended claims and accompanying drawings, where:

Figure 1:
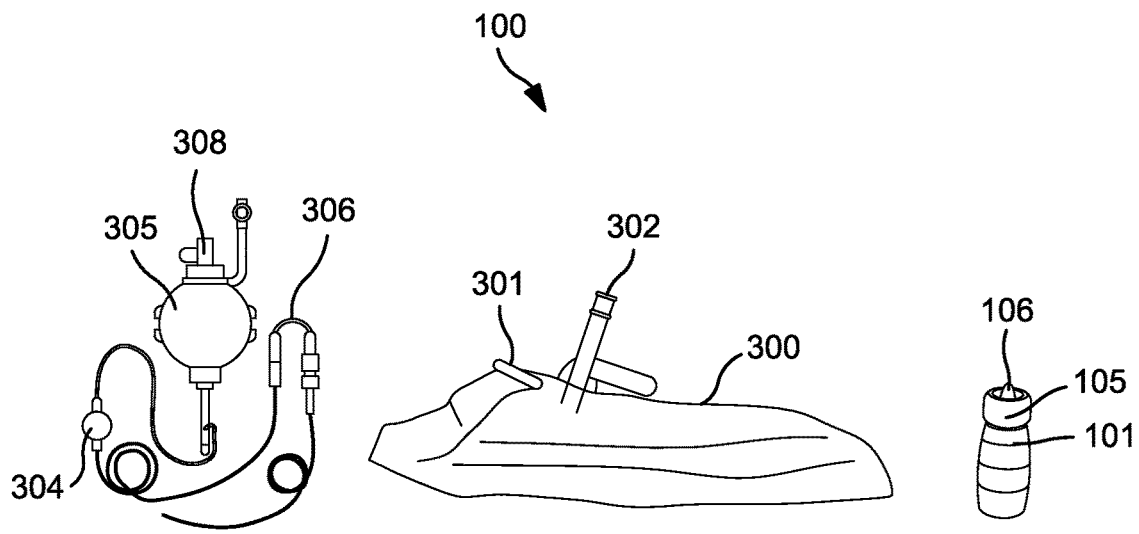
FIG. 1 provides a perspective view of the various components of the wound dressing system of the present disclosure.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

It is to be understood by one of ordinary skill in the art that the present discussion is a description of exemplary aspects only, and is not intended as limiting the broader aspects of the present disclosure. Additionally, the patents and patent applications described or listed herein are incorporated by reference to the extent they do not conflict herewith.

Figure 6:
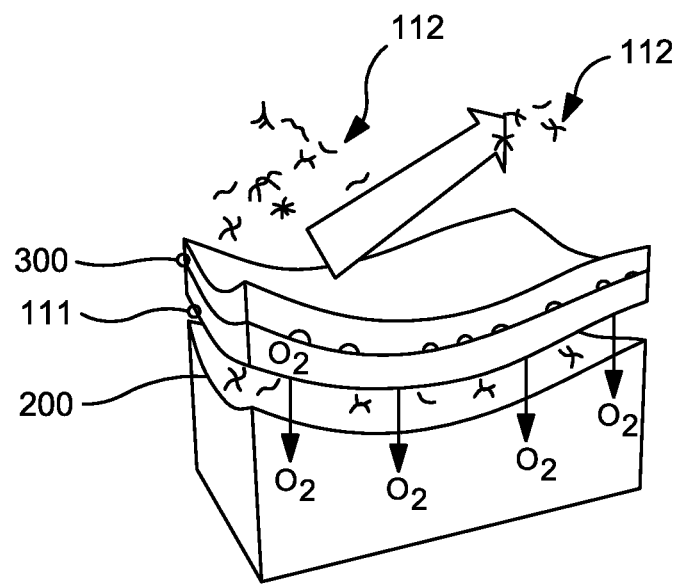
FIG. 6 schematically illustrates the protective and oxygen-generating characteristics of the conformal cover of the present disclosure.

The wound dressing system integrates multiple known-effective actives and wound dressing materials and provides the revolutionary addition of healing oxygen in a small, convenient, stable package. Currently severely injured limbs are wrapped with gauze and in some cases, covered with plastic wrap. This provides an environment where microbes can flourish and tissue dies. The wound dressing system described herein will not only provide an environment that suppresses microbe proliferation, but it also promotes tissue health via the presence of oxygen. The wound dressing system includes a conformal cover that provides oxygen-enriched fluid that preserves damaged tissue and a number of other medicaments and substances to preserve tissue and to promote tissue healing. The protective and oxygen-generating characteristics of the conformal cover are schematically illustrated in FIG. 6 and are discussed in more detail below. Generally, prior to use, the conformal cover is stored inside a package that can also contain a bioactive powder, where the bioactive powder is stored in a foil pack or other container separate from the conformal cover until it is ready for use. Further, an oxygen-generating liquid is contained in an infusion pump or a suitable containment device until ready for use as another component of the traumatic wound dressing system of the present disclosure.

As shown in FIG. 1, the wound dressing system 100 includes a multi-purpose conformal cover 300 that includes a specialized barrier/containment material to protect the wrapped wound in the field environment as well as one or more fluid ports 302 to drain excessive fluids or infuse a bioactive liquid 305 including hydration fluid and/or active agents such as medicaments, oxygen precursors, etc. Further, the conformal cover 300 can include integrated cinch cords 301 requiring no further fixators. The amount of compression and support provided via application of the conformal cover 300 is user controlled and can be manually adjusted after application. In addition, the conformal cover can resist tear propagation.

The large size of the conformal cover 300 and inclusion of cinch cords 301 facilitates the ability of the cover to conform to wound sites of various shapes and sizes. The conformal cover 300 can also be used as a barrier wrap for torso wounds. Further, the conformal cover 300 can be self-opening, which can, for instance, allow for containment of an entire limb with minimal manipulation. The conformal cover 300 can also act as a vapor barrier to further increase hydration while also providing ports for drainage of an excess fluid.

The conformal cover 300 of the traumatic wound dressing system 100 of the present disclosure can be used to completely encase a wounded appendage. In one embodiment, the conformal cover 300 can be in the form of a sleeve and can be equipped with elastic cinch cords 301 throughout (see FIG. 2(c)), which, when tightened or cinched, facilitate the application of compression and allow conformation to the wound. Alternatively, the cover can also be cut along the length and used to wrap a wound if needed.

The wound dressing system 100 can also integrate with the multi-purpose conformal cover 300 an infusion pump 304 (e.g., a manual, elastomeric infusion pump) for fluid and medication delivery from a bag 308 or other suitable fluid containment device via tubing 306 for up to 72 hours. In addition, antimicrobial drugs can be delivered in a controlled and local manner via the infusion pump 304. In other aspects, pain medication can be delivered locally via the pump 304 integrated in the conformal cover 300. Additionally, saline can be delivered before removing the conformal cover 300 via the pump 304 and fluid port(s) 302 or the ports alone 302 to increase hydration or to aid in removal of wound exudate or debris. For instance, the fluid port(s) 302 can be used to remove excess wound drainage manually or via vacuum. These fluid port(s) 302 also have an integrated open cell foam pad built into the cover to promote fluid removal without further tissue injury. Finally, the pump 304 can be used to deliver other suitable active agents, specific growth promoters/inhibitors, etc. in the form of a bioactive liquid 305. For instance, the infusion pump 304 can include a liquid with hemostatic agents, broad spectrum antimicrobial agents, hemostatic agents, biotoxin sequestrants, pain medication, debridement agents, oxygen precursors, etc.

Controlled, local drug delivery is intended to treat and stabilize damaged tissue, avoid infection, and/or allow for rapid and complete debridement at a later time. The pump 304 can be lightweight and can be disposable. This infusion pump is further demonstrated and described in the following documents, all of which are incorporated by reference to the extent they do not conflict herewith: U.S. Pat. No. 8,505,545 to Conquergood, et al.; U.S. Pat. No. 8,439,862 Patent No. to Massengale; and U.S. Pat. No. 8,308,688 to Valle, et al.

Further, in addition to or in combination with the bioactive liquid 305, the traumatic wound dressing system 100 can include a bioactive powder 111 (see FIG. 2(*b*)), which can include hemostatic agents, antimicrobial agents, biotoxin sequestrants, pain medication, debridement agents, oxygen catalysts, etc. as described in more detail below. In this manner, the traumatic wound dressing system 100 can provide oxygen enriched fluid to a wound site that can preserve damaged tissue, a hemostatic agent to reduce blood loss, a broad spectrum antimicrobial agent to reduce the risk of infection, and a neutral surfactant system to enhance debridement once the wound is cared for at an aid station. The bioactive powder 111 can be contained within a bioactive powder container 101. The powder container 101 can be in the form of a sealed foil pack or any other suitable compartment/chamber. Further, a powder dispenser 106 can be located at an end of the powder container 101. The powder dispenser 106 can be in the form of a shaker, nozzle, sprayer, or any other suitable mechanism for dispensing the bioactive powder 111. The bioactive powder 111 can ultimately be applied directly to a wound or wound site by, for instance, rupturing the sealed foil (not shown) of the powder container 101 when the twist cap 105 is twisted.

Moreover, the conformal cover 300 itself can be impregnated with a nanoparticle metal (e.g., nanoparticle silver) or a metal (e.g., silver) in any other suitable form. The metal can act as both an oxygen catalyst to generate oxygen from the introduced oxygen precursor/reactant liquid that is introduced upon application of the traumatic wound dressing system to a wound site, although it is also to be understood that the metal can also act as an antimicrobial.

As shown in FIG. 6, when the traumatic wound dressing system is in use and has been applied to a wound site 200, the combination of the coating of the bioactive powder 111 around the wound site 200 and the application of the conformal cover 300 provides a barrier to prevent or reduce the introduction of microbes 112 or other contaminants into the wound and also provides oxygen-enriched fluid that can preserve damaged tissue. In use, the wound dressing system can also provide a hemostatic agent, a biotoxin sequestrant, a broad spectrum antimicrobial, pain medication, compression, wound exudate absorbency, and a neutral surfactant system to enhance debridement of the wound site once care is rendered at an aid station.

In one example of the use of this traumatic wound dressing system 100 of the present disclosure, a severe limb injury (e.g., avulsion, amputation, laceration, compound fracture, severe burn, degloving, and/or severe abrasion) occurs in theater (i.e., a large area of military operations). A user (e.g., corpsman, medic, first responder, etc.) can then remove the lightweight, compact traumatic wound dressing system of the present disclosure from his/her kit. The user can then assess the wound to determine which components of the wound dressing system are needed and then can use and/or apply the various components of the wound dressing system 100 as discussed below and as shown in FIGS. 2(*a*) through 2(*c*).

Figure 2A:
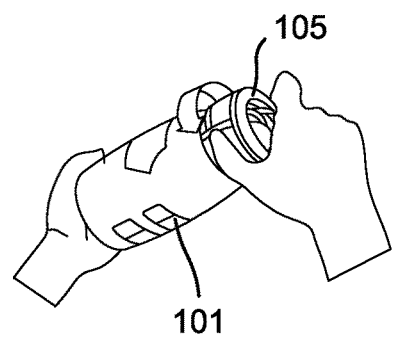
FIGS. 2(a) through 2(c) illustrate the steps for using the wound dressing system of the present disclosure.
Figure 2B:
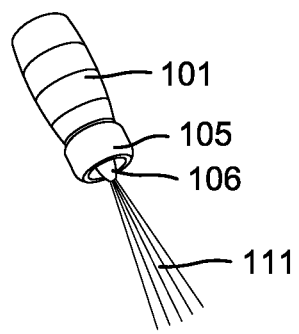
Figure 2C:
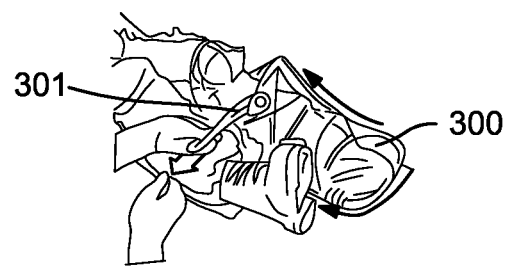

First, as shown in FIG. 2(*a*), after the user has removed the traumatic wound dressing system 100 from its protective packaging, the user can hold the bioactive powder container 101 and twist the twist cap 105 to expose the bioactive powder 111 (see FIG. 2(*b*)) contained inside the bioactive powder container 101. For instance, the twisting action can peel open the foil seal of the bioactive powder container 101 that protects the bioactive powder 111 prior to use.

Next, as shown in FIG. 2(*b*), the user can squeeze or compress the bioactive powder container 101 to activate and thus distribute the powder 111 in a controlled manner onto a wound site 200 (see FIG. 6). The powder 111 can contain oxygen catalysts for use in generating oxygen, as well as hemostatic and antimicrobial components to treat damaged tissue, avoid infection, and prevent further tissue damage.

Next, as shown in FIG. 2(*c*), a conformal cover 300 can be placed over a wound site 200 (see FIG. 6) and the powder 111 that may have been applied to the wound site 200. Once the conformal cover 300 is opened, it can be positioned over the wound site (e.g., a stump portion of an amputated limb), and its cinch straps 301 can then be pulled to secure the conformal cover 300 around the wound site. The multipurpose conformal cover 300 can protect the wound site in the field environment and can also provide ports for removal of excess fluid from the wound or for the infusion of bioactive liquids or fluids, etc. into the wound site to stabilize and protect the wound site during transport. As discussed above, a pump 304 (e.g., a manual infusion pump) and tubing 306 can be used to provide bioactive liquids 305 and other medications to the wound site for a time period of up to 72 hours.

It should be noted that wound dressing in the field is performed primarily at night, under chaotic conditions, or both. Current systems including multiple, separate items tend to be dumped on the ground or splayed in a dirty environment for quick access. As an example of use of the traumatic wound dressing system of the present disclosure in the field, a medic can place the conformal cover over a wound site (e.g., a wounded appendage) and can then pull the cinch cords, which allows the medic to fully encase the wound site and apply compression where needed. The conformal cover can be made from a material that will create a barrier between the wound site and the elements and that is puncture resistant. The medic can then connect the elastomeric infusion pump to a fluid infusion/drainage port on the bag to infuse fluid into the conformal cover and in contact with the wound site. The pump can contain pain medication, antibiotics, or any other substances described herein. Removal of the conformal cover is similar to removing gauze; the conformal cover is single-use only and is disposed after use. It should also be noted that the conformal cover of the present application can be used separately from or in conjunction with the bioactive wrap described in co-pending U.S. Provisional Application Ser. No. 61/931, 166, filed on Jan. 24, 2014. The conformal cover 300 can be packaged separately or together with the bioactive wrap depending on the intended use.

The conformal cover, bioactive powder, and liquid components of the traumatic wound dressing system of the present disclosure are discussed in more detail below.

1. Conformal Cover

As discussed above, the traumatic wound dressing system of the present disclosure includes a conformal cover. The conformal cover can be absorbent and can have elastic properties that provide enhanced compression benefits by applying pressure to immobilize the wound site and minimize minor bleeding. In one embodiment, the conformal cover can be impregnated with a nanoparticle metal (e.g., nanoparticle silver), which can serve as an oxygen catalyst to generate oxygen when the oxygen precursor liquid that is introduced from the fluid bag or other containment device comes into contact with the conformal cover, as discussed in more detail below. In another embodiment, the oxygen catalyst can be any other suitable oxygen catalyst, such as a carbonate (e.g., sodium bicarbonate), a copper compound, catalase, peroxidase, manganese dioxide, iodide, or potassium iodine, for example.

Figure 3:
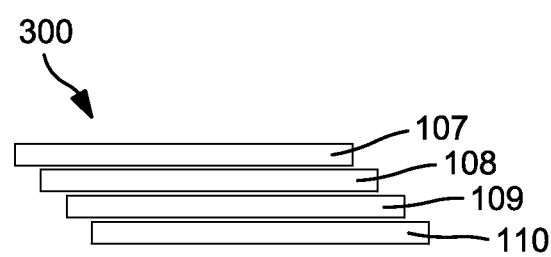
FIG. 3 illustrates schematically a multilayer composite structure of the conformal cover of the present disclosure.

The conformal cover can be formed from a multilayer nonwoven composite material that provides properties similar to woven LYCRA™ fabrics, with the durability and cost of a nonwoven material. The components of one multilayer conformal cover contemplated by the present disclosure are illustrated in FIG. 3. For example, the conformal cover 300 can include a skin or mucosa contacting inner absorbent layer 107, and an outer protective layer 110, where the absorbent layer 107 contacts a wound site and the outer protective layer 110 is exposed to the outside environment upon application of the conformal cover 300 around a wound site. Further, the conformal cover 300 can also include a breathable barrier layer 108 and an elastic layer 109. The various conformal cover 300 components and other components of the traumatic wound dressing system 100 that can be used in conjunction with the conformal cover 300 are described in Table 1 below.

The outer protective layer 110 further protects against bacteria and solid particle penetration through size exclusion, reducing the risk of infection from the environment and the spread of bacteria from the wound to the surrounding area.

Meanwhile, the skin contacting, inner absorbent layer 107 of the conformal cover, which is the layer of the conformal cover positioned adjacent the wound site, provides optimum air and water vapor transport, delivering comfort and thermal management while providing absorbency to control of minor bleeding and wound exudate management. The absorbent layer 107 of the conformal cover can be coated with surfactants to enhance diffusion of the liquid hydrogen peroxide from the bag 308 or other fluid containment device to the trapped nanoparticle metal (e.g., nanoparticle silver) that may be present on various layers of the cover. The surfactant coating can also allow for direct migration of exudates to the absorbent core. Additionally, the inner absorbent layer 107 can be tailored such that it is non-stick to skin or mucosa.

The combination of the outer protective layer 110 and the inner absorbent layer 107 ultimately provides a soft, lint-free, non-irritating feel against skin and mucosa. Further, it is to be understood that both the outer protective layer 110 and the inner absorbent layer 107, and any layers positioned there between, can be impregnated with nanoparticle metal (e.g., nanoparticle silver) which can be employed as a catalyst to generate oxygen from a liquid precursor (e.g., a

TABLE 1

Description and Function of Multilayer Conformal Cover

| Component | Function | Core Technology |
|---|---|---|
| Absorbent wicking layer | Control bleeding<br>Physically protect | U.S. Pat. No. 6,103,647<br>U.S. Pat. App. Pub. No. 2003/0040691 |
| Breathable/barrier layer | Water/air transfer<br>Moisture balance | U.S. Pat. App. Pub. No. 2008/0108268<br>U.S. Pat. No. 6,794,024<br>U.S. Pat. No. 6,045,900 |
| Elastic layer | Compression<br>Conformability | U.S. Pat. App. Pub. No. 2003/0040691<br>U.S. Pat. No. 6,015,764<br>U.S. Pat. No. 6,111,163 |
| Outer protective layer | Tensile strength, tear and puncture resistance<br>Controlled moisture barrier | U.S. Pat. App. Pub. No. 2008/0108268<br>U.S. Pat. No. 6,045,900 |
| Nanoparticle Metal (e.g. nanoparticle silver) | Catalyst to generate oxygen<br>microbial control | U.S. Pat. No. 8,203,029<br>U.S. Pat. No. 8,361,553<br>U.S. Pat. No. 7,576,255<br>U.S. Pat. App. Pub. No. 2004/0010215 |
| Surfactant | Wettability | U.S. Pat. No. 7,666,824 |
| Elastomeric Pump with Catheter | Drug and Fluid Delivery | U.S. Pat. No. 6,981,967<br>U.S. Pat. No. 6,936,035<br>U.S. Pat. No. 8,308,688<br>U.S. Pat. No. 7,465,291<br>U.S. Pat. No. 7,438,711<br>U.S. Pat. No. 7,547,302<br>U.S. Pat. No. 7,527,609<br>U.S. Pat. No. 7,569,045<br>U.S. Pat. No. 8,328,771<br>U.S. Pat. No. 7,959,623 |
| Drainage Port with Integrated Open Cell Foam Pad | Wound Drainage | U.S. Pat. No. 5,730,994<br>U.S. Pat. No. 5,807,563 |

The outer protective layer 110 can provide tensile strength and tear and puncture resistance with adjustable coverage area. The conformal cover provides adjustable levels of compression force due to the retraction forces inherent in the elastic components of the web. The conformal cover provides comfort and conformability to control bleeding, physically protect the wounded limb, and preserve injured tissue.

reactant such as peroxide) that can be introduced before, during, or after the conformal cover is applied to a wound site. To apply the nanoparticle metal, the conformal cover can be treated in a converting process with nanoparticle metal (e.g., nanoparticle silver), and can also be treated with various surfactants, etc. to tailor the functionality of this material for optimum battlefield use. Furthermore, when nanoparticle silver is utilized in such layers, it provides for additional protection against microbial contamination as described above. The catalytic reaction of the hydrogen peroxide with silver occurs at the location of the nanoparticles trapped in the conformal cover 300. The silver that is released for antimicrobial action is at levels below that associated with argyria due to the dissolution rate design of the silver nanoparticles.

The conformal cover 300 and its components are further demonstrated and described in the following documents, all of which are incorporated by reference to the extent they do not conflict herewith: U.S. Pat. No. 8,475,560 to Gann, et al.; U.S. Pat. No. 8,293,965 to McMaken, et al.; U.S. Pat. No. 7,642,397 to Cohen, et al.; U.S. Pat. No. 7,422,712 to DeLucia, et al.; U.S. Pat. No. 5,030,375 to Sigl, et al.; U.S. Patent Application Publication No. 2002/0111576 to Greene, et al.; U.S. Patent Application Publication No. 2003/0127767 to Potts, et al.; U.S. Patent Application Publication No. 2007/0141130 to Villaneuva, et al.; U.S. Pat. No. 6,348,258 to Topolkaraev, et al.; U.S. Pat. No. 4,798,603 to Meyer, et al; U.S. Pat. No. 6,172,276 to Hetzler, et al.; U.S. Pat. No. 6,627,564 to Morman, et al.; U.S. Patent Application Publication No. 2001/0031938 to DeLucia, et al.; U.S. Patent Application Publication No. 2014/0276513 to MacDonald, et al.; U.S. Patent Application Publication No. 2007/0003603 to Karandikar, et al.; U.S. Patent Application Publication No. 2012/0322903 to Karandikar, et al.; U.S. Patent Application Publication No. 2002/0006887 to Radwanski, et al.; U.S. Patent Application Publication No. 2004/0010215 to Gibbins, et al.; U.S. Patent Application Publication No. 2007/0293800 to McMaken, et al.; U.S. Patent Application Publication No. 2009/0035342 to Karandikar, et al.; U.S. Patent Application Publication No. 2012/0183674 to Bonn-Savage, et al.; U.S. Patent Application Publication No. 2007/0254044 to Karandikar, et al.; and U.S. Patent Application Publication No. 2010/0190004 to Gibbins, et al.

2. Powder

The bioactive powder of the wound dressing system of the present disclosure can be applied directly to the wound or wound site and can include one or more of antimicrobial agents, hemostatic agents, biotoxin sequestrants, pain medication, debridement agents, and oxygen catalysts such as a nanoparticle metal (e.g., nanoparticle silver), a carbonate (e.g., sodium bicarbonate), a copper compound, catalase, peroxidase, manganese dioxide, iodide, potassium iodine, etc. The bioactive ingredients may be incorporated into, integrated with, or included in a biocompatible carrier. Further, the biocompatible carrier itself may have bioactive properties.

The bioactive powder composition can treat and stabilize damaged tissue, stop bleeding, avoid infection, neutralize biotoxins, and allow for rapid and complete debridement of the wound site at a later time. The powder is uniquely beneficial in that it can be applied to most wound shapes and depths and quickly sets up as a flexible barrier by absorbing the wound exudate and forming a hydrogel seal on the wound bed. The resulting hydrogel can also maintain a good balance of moisture in the wound bed. The hydrogel powder can also deliver antimicrobial agents and/or other bioactives to the wound site for wound preservation and healing. Further, the hydrogel powder can be easily removed by gentle irrigation of the wound area with saline. Active agents that can be included in the bioactive powder include antimicrobial agents, hemostatic agents, biotoxin sequestrants, pain medication, and debridement agents such as those described in Table 2 and discussed in more detail below.

TABLE 2

Description and Function of Bioactive Powder Components

| Ingredient | Function | Core Technology |
|---|---|---|
| Polyhexamethylene Biguanide (PHMB) | Broad Spectrum Antimicrobial | U.S. Pat. No. 8,551,517 U.S. Pat. App. Publication No. 2007/0048345 U.S. Pat. App. Publication No. 2010/0190004 |
| Aluminum Chloride, Kaolinite, Mineral Zeolite, or Microfibrillar Collagen | OTC Topical Hemostatic Agents | DRYSOL ™ and XERAC ™ AC by Person & Covey CERTAINDRI ™ by DSE Healthcare AVITENE ™ Flour by Davol HELITENE ™ by Integra INSTAT ™ by Ethicon |
| Lidocaine, Benzocaine, or Prilocaine | OTC Local Analgesic | BIOPELLE ™ by Ferndale Laboratories |
| Chlorhexidine Gluconate (CHG) | Preservative Antimicrobial | U.S. Pat. App. Pub. No. 2007/0048345 |
| Biocompatible Carrier | Rheology Modifier Absorbent Moisture Control | U.S. Pat. No. 7,335,713 U.S. Pat. No. 6,822,135 U.S. Pat. No. 8,679,523 U.S. Pat. No. 8,901,188 U.S. Pat. App. Publication No. 2012/265124 PCT/US2014/067530 Caprolactone Urethane Poly(lactic Acid) Diol Urethane Poly(ethylene glycol) Urethane Hydroxybutyric acid urethane |
| Modified Clay | Rheology Modifier Biotoxin Sequestration | U.S. Pat. No. 6,485,733 U.S. Pat. No. 6,517,848 |
| Structured Surfactants | Active Migration Aid Debridement Aid | U.S. Pat. No. 7,666,824 |
| Sodium Carbonate | Neutralizer | — |
| Citric Acid | pH Modifier | — |
| Nanoparticle Metal (e.g., nanoparticle silver) | Antimicrobial and Oxygen Catalyst | U.S. Patent App. Pub. No. 2007/0003603 U.S. Pat. No. 8,203,029 U.S. Pat. No. 8,361,553 |

TABLE 2-continued

Description and Function of Bioactive Powder Components

| Ingredient | Function | Core Technology |
|---|---|---|
| | | U.S. Pat. No. 7,576,255<br>U.S. Pat. App. Pub. No. 2004/0010215 | a. Antimicrobials

Any suitable antimicrobial agent is contemplated for use in the traumatic wound dressing system of the present disclosure. The use of antimicrobial agents is further demonstrated and described in the following documents, all of which are incorporated by reference to the extent they do not conflict herewith: U.S. Patent Application Publication No. 2007/0048344 to Yahiaoui, et al.; U.S. Patent Application Publication No. 2007/0048345 to Huang, et al.; U.S. Patent Application Publication No. 2007/0048356 to Schorr, et al., U.S. Patent Application Publication No. 2006/0140994 to Bagwell, et al.; U.S. Pat. No. 8,203,029 to Gibbins, et al.; and U.S. Pat. No. 8,551,517 to Hoffman, et al. Particular antimicrobial agents contemplated by the present disclosure are discussed in more detail below.

Polyhexamethylene Biguanide (PHMB)

One antimicrobial agent contemplated for use in the traumatic wound dressing system of the present disclosure is polyhexamethylene biguanide (PHMB). PHMB (i.e., polihexanide) is an antiseptic that can be used for wound care applications, although it has a long history of being used in cosmetics, for example in contact lens cleaning solutions, wet wipes, and the like. PHMB is available both as a cleansing solution (PRONTOSAN™, B. Braun) and in biocellulose dressings such as SUPRASORB™ X+PHMB (Lohmann and Rauscher). At a concentration of 0.3% (for example, in SUPRASORB™ X+PHMB) and of 0.1% (for example, in PRONTOSAN™), PHMB has proved to be non-cytotoxic and non-irritant, with a very low risk of sensitization. PHMB has been found to be effective against a broad spectrum of bacteria, aerobic as well as anaerobic, and also against fungi, molds, and yeasts, and has a proven effect against methicillin-resistant *Staphylococcus aureus* (MRSA) and vancomycin-resistant enterococcus (VRE).

Tests have been performed on *Staphylococcus aureus* to investigate the potential risks of this bacterium developing resistance to PHMB; the risk was found to be very low. An additional positive influence on the inflammatory process of wound healing, especially in infected or critically colonized wounds, has been the binding of inflammatory parameters such as free radicals, which demonstrates PHMB's antioxidative potential. The clinical effect of using PHMB in some non-healing wounds has been promising.

PHMB is a linear polymer comprised of a hydrophobic backbone with attached chains that make it highly water soluble. It is active against both gram-negative and gram-positive bacteria, as well as fungi. This activity is not generally affected by production of betalactamase by microorganisms, or by organic matter such as serum, blood, or wound fluid. The broad spectrum activity of PHMB has been demonstrated in studies with gauze dressings containing PHMB. PHMB is a membrane-active agent whose antimicrobial effect depends on disruption of the microbial cytoplasmic membrane and leakage of macromolecular components. The molecule binds to the surface of the bacterial cell membrane and causes reorganization of the membrane in a manner that prevents removal of the antimicrobial agent. This mode of action makes it unlikely that microorganisms can develop resistance.

Studies have compared treatment with a polihexanide-containing biocellulose wound dressing (BWD+PHMB) versus silver dressings (Ag) in painful, critically colonized (wounds-at-risk) or locally-infected wounds. Both BWD+PHMB and AG have been shown to be effective in reducing pain and bacterial burden. However, BWD+PHMB was significantly faster and better in removing the critical bacterial load, which makes such a dressing an attractive therapeutic option separately or in conjunction with silver to treat critically colonized and locally-infected wounds.

The use of PHMB as an antimicrobial agent is further demonstrated and described in the following documents, all of which are incorporated by reference to the extent they do not conflict herewith: U.S. Patent Application Publication No. 2007/0048344 to Yahiaoui, et al.; U.S. Patent Application Publication No. 2007/0048345 to Huang, et al.; U.S. Patent Application Publication No. 2007/0048356 to Schorr, et al; U.S. Patent Application Publication No. 2006/0147502 to Koenig, et al; U.S. Patent Application Publication No. 2007/0134303 to Yahiaoui, et al.; U.S. Patent Application Publication No. 2009/0014009 to Chen, et al.; U.S. Patent Application Publication No. 2006/0067964 to Koenig, et al.; U.S. Patent Application Publication No. 2009/0099532 to Cuevas, et al.; U.S. Patent Application Publication No. 2009/0099531 to Griesbach, III, et al.; U.S. Patent Application Publication No. 2007/0149435 to Koenig, et al.; U.S. Patent Application Publication No. 2010/0190004 to Gibbins, et al.; U.S. Patent Application Publication No. 2007/0044801 to Mathis, et al.; and U.S. Patent Application Publication No. 2006/0140994 to Bagwell, et al.

Chlorhexidine

Another antimicrobial agent or antiseptic contemplated for use in the traumatic wound dressing system of the present disclosure is chlorhexidine, which is a biguanide antiseptic. Chlorhexidine has been commonly used in disinfectant and antiseptic solutions. Chlorhexidine antiseptic solutions are used mainly in urology, gynecology, dentistry, and in the treatment of wounds. It is highly bactericidal. Concentrations around 0.02% can be used for wound irrigation. In other studies, chlorhexidine has been shown to decrease wound healing time. Chlorhexidine rinses have also been shown to be effective in reducing microbial complications when used perioperatively. It is produced in two forms: a 0.05% dilution for wound cleansing and a 4% solution for use as a surgical skin preparation and hand scrub. Recently, 2% solutions have been made available for surgical skin preparation.

Chlorhexidine gluconate (CHG) has been used for more than 30 years in the clinical setting. It has a high level of antimicrobial activity, low toxicity, and strong affinity for binding to the skin and mucous membranes. It can impart its antimicrobial activity at the membrane level, damaging both outer and inner bacterial membranes, causing leakage and possibly disrupting membrane potentials critical for ATP generation. It disrupts the microbial cell membrane and precipitates the cell contents. CHG at a concentration between 0.5% and 4% is more effective against gram-positive than gram-negative bacteria and has less activity against fungi and tubercle bacilli. It is inactive against bacteria spores, except at elevated temperatures. Numerous studies indicate that CHG is not absorbed through the skin and has a low skin irritancy potential. However, CHG should not come into contact with eyes, the middle ear, or meninges.

The use of CHG as an antimicrobial agent is further demonstrated and described in the following documents, all of which are incorporated by reference to the extent they do not conflict herewith: U.S. Patent Application Publication No. 2007/0048345 to Huang, et al.; U.S. Patent Application Publication No. 2004/0120915 to Yang, et al.; U.S. Patent Application Publication No. 2006/0003649 to Runge, et al.; U.S. Patent Application Publication No. 2006/0036222 to Cohen, et al.; U.S. Patent Application Publication No. 2006/0036223 to Baldwin, et al.; and U.S. Patent Application Publication No. 2006/0140994 to Bagwell, et al.

Silver

Another antimicrobial agent contemplated for use in the traumatic wound dressing system of the present disclosure is silver. The therapeutic potential of silver has long been recognized. Due to the broad bactericidal action of silver and the understanding that wound healing is impaired when bacterial levels surpass a particular threshold, multiple silver-based products have been developed to aid in wound healing. Such products incorporate silver into topical creams (silver sulfadiazine or Silvadene; King Pharmaceuticals, Bristol, Tenn.) or within various types of dressings, including foams (Contreet Ag; Coloplast, Marietta, Ga.), hydrocolloids (Contreet H; Coloplast, Marietta, Ga.), hydrofibers (AQUACEL™ Ag; Covatec, Skillman, N.J.), alginates (SILVERCEL™; Systagenix, Quincy, Mass.), film polymers (ARGLAES™; Medline, Mundelein, Ill.), or a polyethylene mesh with nanocrystalline silver (ACTICOAT™ Flex 7; Smith and Nephew, Hull, UK). These products work through the release of reactive silver cations, [Ag+], which may disrupt components of the bacterial cell wall, inhibit microbial respiratory enzymes and elements of the electron transport chain, and impair the synthesis and function of DNA and RNA.

The use of silver as an antimicrobial agent is further demonstrated and described in the following documents, all of which are incorporated by reference to the extent they do not conflict herewith: U.S. Patent Application Publication No. 2007/0003603 to Karandikar, et al.; U.S. Patent Application Publication No. 2012/0322903 to Karandikar, et al.; U.S. Patent Application Publication No. 2002/0006887 to Radwanski, et al.; U.S. Patent Application Publication No. 2004/0010215 to Gibbins, et al.; U.S. Patent Application Publication No. 2007/0293800 to McMaken, et al.; U.S. Patent Application Publication No. 2009/0035342 to Karandikar, et al; U.S. Patent Application Publication No. 2012/0183674 to Bonn-Savage, et al; U.S. Patent Application Publication No. 2007/0254044 to Karandikar, et al.; U.S. Patent Application Publication No. 2013/0164334 to Quincy, III, et al.; U.S. Patent Application Publication No. 2012/0240728 to Gann, et al.; U.S. Pat. No. 4,856,504 to Yamamoto, et al.; U.S. Patent Application Publication No. 2002/0022050 to Anderson, et al.; U.S. Patent Application Publication No. 2004/0120921 to Quincy, III, et al.; U.S. Pat. No. 6,797,856 to Kolb, et al.; U.S. Patent Application Publication No. 2006/0003649 to Runge, et al.; U.S. Pat. No. 6,020,047 to Everhart; U.S. Patent Application Publication No. 2005/0058711 to Massengale, et al.; U.S. Patent Application Publication No. 2011/0135702 to Hoffman, et al.; U.S. Patent Application Publication No. 2005/0148490 to Krzysik, et al.; U.S. Patent Application Publication No. 2008/0132438 to Hoffman, et al.; U.S. Patent Application Publication No. 2003/0203009 to MacDonald; U.S. Patent Application Publication No. 2010/0190004 to Gibbins, et al.; U.S. Pat. No. 5,599,585 to Cohen; and U.S. Patent Application Publication No. 2007/0044801 to Mathis.

b. Hemostatic Agents

Hemostatic agents are also contemplated for use in the traumatic wound dressing system of the present disclosure and can be used to deliver blood loss prevention and/or coagulation benefits. Useful hemostatic agents include polyacrylate polymers, modified clays, and $CaCl_2$ in a polyacrylate polymer matrix. The use of these and other hemostatic agents is further demonstrated and described in the following documents, all of which are incorporated by reference to the extent they do not conflict herewith: U.S. Pat. No. 7,335,713 to Lang, et al.; and U.S. Pat. No. 6,822,135 to Soerens, et al.

c. Toxin Sequestration Agents

Toxin sequestration agents are also contemplated for use in the traumatic wound dressing system of the present disclosure. Toxin sequestration agents include modified clay technology, as well as any other agents that reduce or eliminate biotoxin interaction with the wound and the surrounding tissue. The use of these and other toxin sequestration agents is further demonstrated and described in the following documents, all of which are incorporated by reference to the extent they do not conflict herewith: U.S. Pat. No. 6,551,607 to Minerath, III, et al.; U.S. Pat. No. 6,521,241 to Minerath, III, et al.; U.S. Pat. No. 6,485,733 to Huard, et al.; U.S. Pat. No. 6,517,848 to Huard, et al.; and U.S. Pat. No. 8,110,215 to Koenig, et al.

d. Pain Medication

Pain medications are well known, and any suitable topical, local, or systemic pain medication known in the art can be used in the traumatic wound dressing system of the present disclosure. Suitable examples include but are not limited to lidocaine, benzocaine, or prilocaine.

e. Debridement Agents

The traumatic wound dressing system of the present disclosure also contemplates the use of one or more debridement agents. Debridement upon reaching an aid station can be enhanced by using debridement agents. Classes of such debridement agents include structured surfactant technology and agents that allow cleaning and debridement of the wound and the surrounding tissue. The use of these and other debridement agents is further demonstrated and described in the following documents, all of which are incorporated by reference to the extent they do not conflict herewith: U.S. Pat. No. 7,268,104 to Krzysik et al.; U.S. Pat. No. 7,666,824 to Krzysik, et al.; U.S. Pat. No. 8,545,951 to Yahiaoui, et al.; and U.S. Pat. No. 6,764,988 to Koenig, et al.

f. Modified Clay

The traumatic wound dressing system of the present disclosure also contemplates the use of a modified clay. The use of modified clays is further demonstrated and described in the following documents, all of which are incorporated by reference to the extent they do not conflict herewith: U.S. Pat. No. 6,551,607 to Minerath, III, et al.; U.S. Pat. No. 6,521,241 to Minerath, III, et al.; U.S. Pat. No. 6,517,848 to Huard, et al.; and U.S. Pat. No. 6,485,733 to Huard et al. In some embodiments, the clays can be organophilically or non-organophilically modified. By an organophilically modified clay it is meant that the naturally occurring charge has been significantly reduced by adding relatively hydrophobic material to the surface of the native material. For instance, modifications to clays have been accomplished using a variety of techniques including derivatization with phenolic, quaternary ammonium, methyl methacrylate compounds. For example, a quaternary ammonium compound that can be used in preparing the organophilic modified clay component of the traumatic wound dressing of the present disclosure can have one or two long-chain substituents, e.g., 14-20 carbon atoms, and two or three short-chain substituents such as methyl groups. One particularly suitable quaternary ammonium compound is dimethyl dihydrogenated tallow ammonium chloride. Because the tallow contains a large proportion of stearic acid, which contains 18 carbon atoms, the resulting clay is often referred to as a quaternium 18 clay, e.g., quaternium 18 bentonite, or quaternium 18 hectorite. The composition and preparation of such organophilic clays is well-known. In one embodiment, the modified organophilic clay for use in the present disclosure is quaternium 18 bentonite. Meanwhile, non-organophilically modified clays are formed by minor other processing modifications, such as the addition of inorganic counter ions, such as mono- and di-valent cations, e.g. lithium, sodium or potassium.

3. Liquid

In addition to including a conformal cover and a bioactive powder component, the traumatic wound dressing system of the present disclosure can also include a liquid component. Prior to use of the traumatic wound dressing system to cover a wound site, the bioactive liquid can be contained in a bag similar to an I.V. bag or any other suitable containment device that can be connected to an infusion pump. The liquid from the bag or other suitable containment device can be infused via a pump into the conformal cover such that the liquid can saturate the interior of the conformal cover before, during, or after application of the conformal to a wound site. The liquid can include one or more of hemostatic agents, antimicrobial agents, biotoxin sequestrants, pain medication, debridement agents, and precursors for oxygen generation (e.g., a reactant such as a peroxide). Hemostatic agents, antimicrobial agents, biotoxin sequestrants, pain medication, and debridement agents are described above with respect to the bioactive powder. In some embodiments, it is contemplated that the liquid component may include a biocompatible carrier for certain ingredients. For example, one or more ingredients may be incorporated into, integrated with or be included in a biocompatible carrier that may be blended or included in the liquid, and the biocompatible carrier itself may have bioactive properties.

The main functions of the liquid can be to provide oxygen to the wound site, to minimize infection at the wound site, and to allow for rapid and complete debridement of the wound site at a later time. In one embodiment, the liquid can be formulated using FDA-approved ingredients and can include one or more of hydrogen peroxide (such as 3.3% hydrogen peroxide), cationic surfactants, stabilizing agents, thickening agents, and preservatives. The liquid composition can also include a hemostatic agent and pain medication such as a local analgesic. The various components of the liquid are described below in Table 3.

TABLE 3

Description and Function of Bioactive Liquid Components

| Ingredient | Function | Core Technology |
|---|---|---|
| Hydrogen Peroxide | Precursor for Oxygen Generation | U.S. Pat. No. 7,160,553<br>U.S. Pat. No. 7,235,263 |
| Structured Surfactants | Active Migration Aid<br>Debridement Aid | U.S. Pat. No. 7,666,824 |
| Sorbitol or Mannitol | Hydrogen Peroxide Stabilizer | U.S. Pat. No. 7,235,263 |
| Polyhexamethylene Biguanide (PHMB) | Preservative<br>Antimicrobial | U.S. Pat. No. 8,551,517<br>U.S. Pat. App. Pub. No. 2007/0048345<br>U.S. Pat. App. Pub. No. 2010/0190004 |
| Biocompatible Carrier | Rheology Modifier<br>Absorbent<br>Moisture Control | U.S. Pat. No. 7,335,713<br>U.S. Pat. No. 6,822,135<br>U.S. Pat. No. 8,679,523<br>U.S. Pat. No. 8,901,188<br>U.S. Pat. App. Publication No. 2012/265124<br>PCT/US2014/067530<br>Caprolactone Urethane<br>Poly(lactic Acid) Diol Urethane<br>Poly(ethylene glycol) Urethane<br>Hydroxybutyric acid urethane |
| Sodium Carbonate | Neutralizer | — |
| Citric Acid | pH Modifier | — |
| Optional Microencapsulated Delivery Vehicle | Optional Encapsulation of hydrogen peroxide | U.S. Pat. No. 8,192,841<br>U.S. Pat. App. Pub. No 2007/0148459 |
| Optional Aluminum Chloride, Kaolinite, Mineral Zeolite, or Microfibrillar Collagen | Optional OTC Topical Hemostatic Agents | DRYSOL ™ and XERAC ™ AC by Person & Covey<br>CERTAINDRI ™ by DSE Healthcare<br>AVITENE ™ Flour by Davol<br>HELITENE ™ by Integra<br>INSTAT ™ by Ethicon |
| Optional Lidocaine, Benzocaine, or Prilocaine | Optional OTC Local Analgesic | BIOPELLE ™ by Ferndale Laboratories |
| Optional Modified Clay | Optional Rheology Modifier<br>Anti-Caking Agent<br>Biotoxin Sequestration | U.S. Pat. No. 6,485,733<br>U.S. Pat. No. 6,517,848 |

4. Oxygen Generation

Another feature of the traumatic wound dressing system of the present disclosure is the ability of the system to generate oxygen within the conformal cover and then subsequently deliver this oxygen to the wound and the surrounding tissue.

The oxygenation needs of the human skin are typically met by the combination of direct oxygen uptake from the ambient air and by tissue oxygenation from the vasculature. Dissolved oxygen is essential at all stages of the wound healing process. Poor tissue oxygenation can result in impaired healing. Chronic wounds are notably hypoxic, with an oxygen tension of 5 to 20 mmHg, compared to an oxygen tension of 30 to 50 mmHg in healthy tissue. In healing tissue, oxygen is required as a substrate for the production of biological energy, resistance to infection, collagen synthesis, blood vessel formation, cell migration, and cell proliferation. In addition, oxygen also serves as a signaling molecule to initiate cell motility and enhance the expression of several pro-inflammatory and angiogenic growth factors. In the human skin, adequate oxygen supply is a balance between proper oxygen transport by the blood and direct uptake from the atmosphere. Therefore, oxygen delivery to the wound is dependent on multiple factors including blood perfusion of the tissue, capillary density, arterial partial oxygen pressure (poxygen), the blood hemoglobin level, and local oxygen consumption. Oxygen is not stored in the tissue and several systemic conditions, including advancing age and diabetes, can endanger its availability. Consequently, it is imperative that upon injury, the healing tissue quickly adapts to continuously meet the oxygen requirements for proper healing and repair. Although the wounded tissue demands high oxygen levels, the overall oxygen needs of a wound differ at the different stages of the wound healing process.

Healthy tissue needs to be able to adjust oxygen delivery when there is an increase in oxygen demand. In the human skin oxygen delivery occurs by diffusion via direct uptake from the atmosphere and from the vasculature, where the oxygen moves from areas of high concentration to areas of low concentration. Satisfactory oxygen supply to the subcutaneous tissue is highly dependent on appropriate oxygen transport through the blood at a sufficient bulk flow rate. During tissue injury, blood supply decreases due to disruption of blood vessels. As a consequence, there is a marked decrease in oxygen delivery. Although the wounded tissue is equipped with all the necessary tools to repair the damage and restore blood supply, there are intrinsic and extrinsic factors that can impair this process, resulting in prolonged oxygen deficiency or chronic tissue hypoxia. Because adequate oxygen supply is essential for successful tissue repair, inability of the wounded tissue to meet oxygen demand can be pathological, resulting in cell death and tissue necrosis.

Therefore, the goal of an oxygen-based therapy for wound care is to fulfill the oxygen demand of the healing tissue and maintain an oxygen concentration near an oxygen tension of about 40 mmHg, which is the average oxygen tension found in healthy, well-perfused tissues. Delivery of oxygen as part of oxygen-based therapy has been used clinically as an effective therapy for wound healing since the 1960s with the administration of systemic hyperbaric oxygen (HBO).

Throughout the years, advancements have been made in the scientific field to improve oxygen-based therapies for wound healing. In recent years, new oxygen delivery technologies have emerged that aim to locally provide oxygen to the wounded tissue at a faster and more efficient way than HBO therapy via topical administration. Clinical results have shown that topical delivery of oxygen to the wounded tissue can enhance the rate of epithelialization, induce extracellular matrix protein synthesis, and the expression of angiogenic factors. It should be understood that topically-delivered oxygen only targets the wounded tissue and, as a result, it does not involve high pressure and does not risk the potential for systemic oxygen toxicity.

Figure 4:
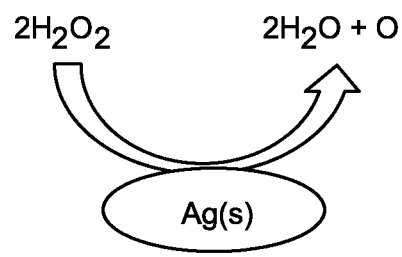
FIG. 4 illustrates the oxygen production associated with a silver-nanoparticle-impregnated conformal cover of the present disclosure.
Figure 5:
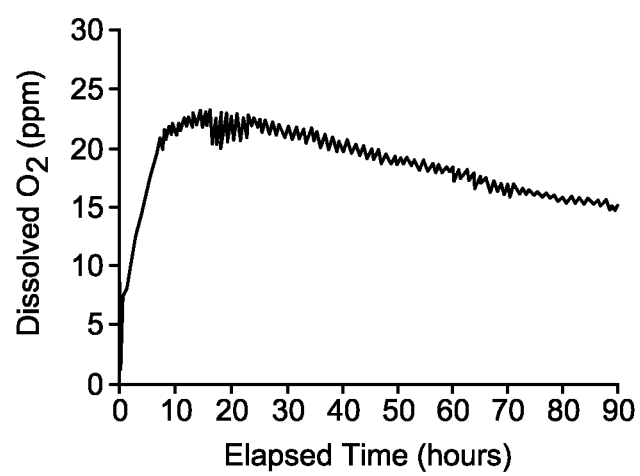
FIG. 5 illustrates the hydrogen peroxide generated oxygen release as a function of time from a polyacrylate polymer.

A wound dressing product as described in U.S. Pat. No. 7,160,553 to Gibbins, et al. and U.S. Pat. No. 8,679,523 to Gibbins, et al. and sold under the name OXYGENESYS™ has been developed that can deliver dissolved oxygen to the wound over an extended period. In this product, oxygen is produced by mixing a reactant (i.e., oxygen precursor) with an oxygen catalyst. The oxygen generation system used in the present application can employs hydrogen peroxide ($2H_2O_2$) as the reactant and silver nanoparticles Ag(s) as the catalyst to produce water ($2H_2O$) and oxygen ($O_2$), as illustrated in FIG. 4, although any other suitable reactant/catalyst combination as discussed in U.S. Pat. No. 7,160,553 to Gibbins, et al. and U.S. Pat. No. 8,679,523 to Gibbins, et al. is contemplated by the present disclosure. Both the nanoparticle silver on the surface of conformal cover and the silver ions released serve to convert the hydrogen peroxide into oxygen. An example of this process has shown that oxygen generated by the catalytic conversion of hydrogen peroxide incorporated into a polyacrylate polymer can be released for over 80 hours, as illustrated in FIG. 5. The hydrogen peroxide reactant acts as an oxygen precursor. Other useful oxygen precursors include mannitol peroxide, urea peroxide, organic peroxides, and combinations thereof. Meanwhile, in addition to nanoparticle silver, other suitable oxygen catalysts can include a carbonate (e.g., sodium bicarbonate), a copper compound, catalase, peroxidase, manganese dioxide, iodide, potassium iodine, etc.

Such a chemistry is employed in the traumatic wound dressing system of the present application. When the system is deployed, oxygen will be generated and trapped between the wound and the hydrogel formed by the bioactive powder. The material design of the hydrogel resulting from coating or spraying the bioactive powder on a wound site as well as the design of the conformal cover ensure that the oxygen will be delivered to the wound over an extended period of time. Although nanoparticle silver has been primarily discussed above, it is to be understood that any other suitable catalyst can be used in the traumatic wound dressing system of the present disclosure. For instance, the catalyst used to generate oxygen can be one or more of other metallic nanoparticles including copper, zinc, nickel, and gold. The use of silver, including silver nanoparticles, as the catalyst also serves the purpose of an additional antimicrobial, as described above.

The wound dressing system of the present disclosure also contemplates the use of a polyacrylamide-based matrix that can release and deliver both dissolved oxygen and silver. The matrix is available as a conformable gel patch or foamed gel and is sold under the OXYGENESYS™ brand name. Other polyacrylic acid-based hydrogel matrices employed herein demonstrate delivery of dissolved oxygen, silver, and bioactives. On contact with the wound surface, the matrix can form a viscous hydrogel allowing for an increased and more consistent concentration of dissolved oxygen to be delivered to the wound bed over many hours.

The polyacrylic acid-based gel can also be converted into a flowable powder, allowing it to be applied to a wound site in dry, powdered form. The unique benefits of the powder is that it can be applied to most wound shapes and depths and quickly sets up as a flexible barrier by absorbing the wound exudate and forming a hydrogel seal on the wound bed. This hydrogel also maintains a good balance of moisture in the wound bed. The hydrogel powder can also deliver dissolved oxygen, antimicrobials, and/or other bioactives as discussed above for wound preservation and healing. When the wound dressing system is removed after use, the powdered hydrogel coating can be easily removed by gentle irrigation of the wound area with gravity fed saline.

An advantage of the oxygen-generating technology described herein is that it can supply continuous oxygen to the wound in a form that has already crossed the gas to liquid interface (as the free, unbound oxygen found in plasma), thus making it readily available for cell consumption. This oxygen-generating technology has proven effective in the transcutaneous delivery of dissolved oxygen beyond a 700 µm thickness of viable human skin, achieving a penetration oxygen level twice the depth of that observed for hyperbaric gaseous oxygen therapy. Furthermore, this technology has shown to positively affect various phases of the wound healing process. Specifically, this oxygen-generating technology has been found to reduce dermal and subcutaneous inflammation as well as bacterial burden in ischemic porcine wounds. Such oxygen-generating technology can also reduce dermal fibrosis and necrosis. Further, this oxygen-generating technology can promote healing when applied to chronic venous stasis ulcers, dehiscent surgical closures, pressure ulcers, and skin flaps. Furthermore, delivery of dissolved oxygen by this oxygen-generating technology wound dressing system can facilitate increase in collagen type I, elastin and fillagrin, in addition to down-regulating inflammatory cytokines and matrix metalloproteinases 1 and 12.

This oxygen-generating technology is further demonstrated and described in the following documents, all of which are incorporated by reference to the extent they do not conflict herewith: U.S. Pat. No. 8,679,523 to Gibbins, et al.; U.S. Pat. No. 7,160,553 to Gibbins, et al.; U.S. Pat. No. 7,235,263 to Koenig, et al.; and U.S. Pat. No. 6,887,496 to Koenig, et al.

The dimensions and values disclosed herein are not to be understood as being strictly limited to the exact numerical values recited. Instead, unless otherwise specified, each such dimension is intended to mean both the recited value and a functionally equivalent range surrounding that value. For example, a value disclosed as "10" is intended to mean "about 10."

All documents cited in the Detailed Description are, in relevant part, incorporated herein by reference; the citation of any document is not to be construed as an admission that it is prior art with respect to the present disclosure. To the extent that any meaning or definition of a term in this written document conflicts with any meaning or definition of the term in a document incorporated by reference, the meaning or definition assigned to the term in this written document shall govern.

While particular aspects of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A wound dressing system comprising:
   a conformal cover, wherein the conformal cover comprises a multilayer material including an outer protective layer, an elastic layer, a breathable layer, and an inner absorbent layer, further wherein the conformal cover includes a fluid port and an oxygen catalyst;
   a container having a powder dispenser and comprising a bioactive powder; and
   an infusion pump configured to deliver a bioactive liquid to the conformal cover via the fluid port, wherein the bioactive liquid includes an oxygen precursor.

2. The system of claim 1, wherein the conformal cover is configured to form a sleeve around the wound site.

3. The system of claim 1, wherein the oxygen catalyst includes a nanoparticle metal, a carbonate, a copper compound, catalase, peroxidase, manganese dioxide, iodide, potassium iodine, or a combination thereof.

4. The system of claim 3, wherein the nanoparticle metal is silver.

5. The system of claim 1, wherein the bioactive liquid further includes a hemostatic agent, an antimicrobial agent, a biotoxin sequestrant, pain medication, a debridement agent, or a combination thereof.

6. The system of claim 1, wherein the oxygen precursor includes a peroxide.

7. The system of claim 6, wherein the peroxide includes hydrogen peroxide, mannitol peroxide, urea peroxide, an organic peroxide, or a combination thereof.

8. The system of claim 1, wherein the oxygen catalyst and the oxygen precursor are configured to form oxygen when combined.

9. The system of claim 1, wherein the bioactive powder includes a hemostatic agent, an antimicrobial agent, a biotoxin sequestrant, pain medication, a debridement agent, or a combination thereof.

10. The system of claim 1, wherein the conformal cover is a nonwoven composite.

11. The system of claim 1, wherein the inner absorbent layer is configured to be positioned adjacent the wound site when the conformal cover is positioned around the wound site.

12. The system of claim 1, wherein the infusion pump is elastomeric.

13. A method of applying a wound dressing system comprising a container that includes a bioactive powder, a bioactive liquid, and a conformal cover to a wound site, the method comprising:
    applying the bioactive powder to the wound site, wherein the bioactive powder is dispensed from the container via a powder dispenser;
    securing the conformal cover around the wound site, wherein the conformal cover comprises a multilayer material including an outer protective layer, an elastic layer, a breathable layer, and an inner absorbent layer, further wherein the conformal cover includes an oxygen catalyst a fluid port; and
    delivering the bioactive liquid to at least an inner layer of the conformal cover via the fluid port, wherein the bioactive liquid includes an oxygen precursor.

14. The method of claim 13, wherein oxygen is formed when the oxygen precursor contacts the oxygen catalyst.

15. The method of claim 13, wherein the oxygen precursor includes a peroxide.

16. The method of claim 13, wherein the oxygen catalyst includes a nanoparticle metal, a carbonate, a copper compound, catalase, peroxidase, manganese dioxide, iodide, potassium iodine, or a combination thereof.

17. The method of claim 13, wherein an infusion pump delivers the bioactive liquid to an interior of the conformal cover.

\* \* \* \* \*